United States Patent [19]

Kazan

[11] 4,136,101

[45] Jan. 23, 1979

[54] PROCESS FOR PREPARING DIALKYL (P-AMINOBENZOYL) GLUTAMATES

[75] Inventor: John Kazan, Bridgewater, N.J.

[73] Assignee: American Cyanamid Company, Stamford, Conn.

[21] Appl. No.: 875,051

[22] Filed: Feb. 3, 1978

[51] Int. Cl.$^2$ .................... C07F 3/06; C07C 101/26
[52] U.S. Cl. .................... 260/429.9; 560/41; 544/260
[58] Field of Search .................... 560/41; 260/429.9

[56] References Cited

U.S. PATENT DOCUMENTS 3,892,801  7/1975  Kazan .................... 260/518 R

OTHER PUBLICATIONS

Lee et al., J. of Medicinal Chem., vol. 17, No. 3, pp. 326–329 (1974).

*Primary Examiner*—James O. Thomas, Jr.
*Assistant Examiner*—G. T. Breitenstein
*Attorney, Agent, or Firm*—Charles F. Costello, Jr.

[57] ABSTRACT

A process for the preparation of dialkyl (p-aminobenzoyl) glutamates is disclosed. Dialkyl (p-Aminobenzoyl) glutamates are useful as intermediates in the synthesis of N-{p-([(2,4-diamino-6-pteridinyl)-methyl]methylamino)benzoyl}glutamic acid, also known as 4-amino-N$^{10}$-methylpteroylglutamic acid. The compound zinc N-(p-methylaminobenzoyl)-L-(+)-glutamate, is also disclosed.

6 Claims, No Drawings

PROCESS FOR PREPARING DIALKYL (P-AMINOBENZOYL) GLUTAMATES

This invention relates to a process for preparing dialkyl (p-aminobenzoyl)glutamates by the use of zinc(p-aminobenzoyl)glutamates. More particularly, this invention relates to the preparation of dialkyl N-(p-methylaminobenzoyl)glutamates by the use of zinc N-(p-methylaminobenzoyl)glutamate.

The dialkyl (p-aminobenzoyl)glutamates prepared by the process of the present invention are represented by formula (I):

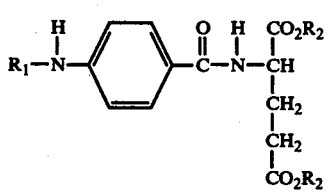

wherein $R_1$ is selected from hydrogen or $C_1$–$C_4$ alkyl and $R_2$ is $C_1$–$C_4$ alkyl.

The preparation of diethyl N-(p-methylaminobenzoyl)glutamate by the reaction of disodium N-(p-methylaminobenzoyl)glutamate with hydrogen chloride and ethanol is disclosed by Cosulich et al. in J. Am. Chem. Soc. 70, 1922 (1948). In this process the reaction is carried out at ambient temperature, the reaction mixture is diluted with water, clarified, and alkalized to pH 7–8 with ammonium hydroxide to precipitate the product which is recovered and purified by recrystallization from water.

The dialkyl (p-Aminobenzoyl)glutamates prepared by the process of the present invention are useful as intermediates in the synthesis of N-{p-([(2,4-diamino-6-pteridinyl)methyl]methylamino)benzoyl}glutamic acid, also known as 4-amino-$N^{10}$-methylpteroylglutamic acid, or methotrexate, a product which is useful for treating certain forms of cancer in humans.

However, the low solubility of the disodium salt in ethanol at ambient temperature greatly reduces the reaction rate. About three days are required to complete the reaction at 25–30° C. Furthermore, the disodium salt is difficult to prepare in a high state of purity.

There is a need for a process for the rapid preparation of dialkyl (p-aminobenzoyl)glutamates in a high state of purity.

There is a special need for a process for the preparation of diethyl N-(p-methylaminobenzoyl)-L-(+)-glutamate which is useful as an intermediate in the preparation of N-p-([(2,4-diamino-6-pteridinyl)methyl]methylamino)benzoyl-L-(+)-glutamic acid which is used for treating certain forms of cancer in humans.

The process for the preparation of an ester represented by formula (I) wherein $R_1$ and $R_2$ are as previously identified comprises reacting a zinc salt of a (p-aminobenzoyl)glutamic acid, represented by formula (II):

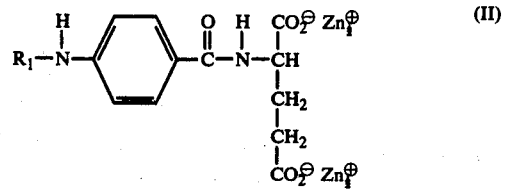

wherein $R_1$ is selected from hydrogen of $C_1$–$C_4$ alkyl, with $C_1$–$C_4$ alcohol, at ambient tempetature in the presence of an inorganic acid to form an ester of formula (I); diluting the reaction mixture with water; clarifying and alkalizing the clarified reaction mixture and to about pH 4–6 to precipitate the ester of formula (I); and, recovering the same.

In the preferred embodiment of this invention the reaction is carried out in ethanol in the presence of hydrogen chloride, and the clarified reaction mixture is alkalized to about pH 5 with concentrated ammonium hydroxide as the alkalizing agent.

In the preferred embodiment of this invention zinc N-(p-methylaminobenzoyl)glutamate is reacted as described above. In the especially preferred embodiment, zinc N-(p-methylaminobenzoyl)-L-(+)-glutamate is reacted.

The process of this invention results in a significant improvement in the purity of the final product because the crystalline nature of the zinc salts allows them to be readily purified. This is not the case with other metal salts which tend to be amorphous or gelatinous. For example, the purity of the zinc N-(p-methylaminobenzoyl)-L-(+)-glutamate is about 80–90% versus about 55–70% for the corresponding disodium salt. In addition to the resulting improved purity of the final product the processing time is greatly reduced with no sacrifice in yield.

In carrying out the improved process of this invention a zinc salt represented by formula (II), which may be dextrorotatory, levorotatory, or a racemic mixture, preferably dextrorotatory zinc N-(p-methylaminobenzoyl)-L-(+)-glutamate, is reacted under essentially anhydrous conditions at ambient temperature, about 20° C to 35° C, with an alcohol having 1 to 4 carbon atoms, such as methanol, ethanol, 2-propanol, 1-butanol, and the like, preferably ethanol, in the presence of an amount of an inorganic acid sufficient to convert all of said zinc salt to the free acid, preferably gaseous hydrogen chloride. The reaction mixture is stirred at ambient temperature for about 3 to 8 hours, preferably about 5 hours, diluted with water, stirred with activated carbon and a filter aid, such as a diatomaceous earth, and filtered to effect clarification.

The clarified reaction mixture is treated with a suitable alkalizing agent such as sodium carbonate, ammonium hydroxide, sodium hydroxide, potassium hydroxide, and the like, preferably concentrated ammonium hydroxide, at about 20° C to 35° C, preferably about 25° C to 30° C, to adjust the pH of the reaction mixture to about 4 to 6, preferably about 5. The resulting precipitate is then recovered by suitable means, washed with water and dried to obtain the desired compound of formula (I).

The following examples illustrate the process of this invention.

EXAMPLE 1

Preparation of Aqueous Solution of Disodium N-(p-Methylaminobenzoyl)-L-(+)-glutamate A 40% aqueous solution of methylamine (522 grams; 6.74 moles) is added to N-(-p-chlorobenzoyl)-L-(+)-glutamic acid monohydrate (370 grams; 1.219 moles) and the mixture is stirred to completely dissolve the acid. Finely pulverized cuprous chloride (42 grams) is added and the mixture is again stirred to effect complete dissolution. The reaction mixture is then added to an autoclave using 40% aqueous methylamine (250 grams; 3.23 moles) to rinse the material into the autoclave which is then sealed. After heating the reaction mixture at 125–127° C for 7 hours, the vessel is cooled to room temperature, vented, and the contents removed therefrom. The vessel is rinsed with water and sodium sulfide (64 grams) is added to the reaction mixture plus rinsings. The reaction mixture is stirred until the blue color is discharged, and a filter aid is then added thereto; after stirring for 5 minutes the mixture is filtered. The filter cake is washed with distilled water and the filtrate plus washings is concentrated under reduced pressure to remove methylamine and hydrogen sulfide. The resulting solution is then diluted with water to the volume prior to concentration.

EXAMPLE 2

Preparation of Zinc N-(p-Methylaminobenzoyl-L-(+)-glutamate

Concentrated hydrochloric acid is added to the solution of Example 1 to adjust the pH to 2.3–2.5. Zinc chloride (171 grams; 1.25 moles) is added to the reaction mixture and the resulting solution is stirred while sodium hydroxide is added to adjust the pH to 5.0–5.2.

The resulting precipitate is recovered by filtration, washed with water, and dried in a vacuum oven to obtain zinc N-(p-methylaminobenzoyl-L-(+)-glutamate (190 grams real; 45% of theoretical).

An analytically pure sample is obtained by dissolving the crude product in aqueous hydrochloric acid (pH 2.0–2.5) and adding sodium hydroxide to a constant pH 3.0. The resulting crystals are recovered by filtration, washed with water, and dried.

Calculated for $C_{13}H_{14}N_2O_5Zn$ : C, 45.44; H, 4.11; N, 8.14; Zn, 19.02. Found[a]: C, 45.30; H, 4.36; N, 8.20; Zn, 19.01.

(a) Values obtained after correction for 0.84% moisture in the sample.

EXAMPLE 3

Preparation of Diethyl N-(p-Methylaminobenzoyl-L-(+)-glutamate

Anhydrous hydrogen chloride (26 grams) is added to anhydrous ethanol (250 mls.) by surface absorption at 0–5° C. Dry zinc N-(p-metylaminobenzoyl-L-(+)-glutamate (57 grams; 0.166 mole) is rapidly added thereto while stirring and maintaining the temperature below 30° C. Upon completion of the addition the reaction mixture is stirred at 25–30° C for 5 hours and then diluted with an equal volume of water. Activated carbon (6.5 grams ) and a filter aid (3.5 grams; Hyflo ®Super-Cel) are added thereto and after stirring at 25–30° C for ½ hour the reaction mixture is clarified by filtration. Concentrated ammonium hydroxide is added to adjust the filtrate to pH 5 and precipitate the product. The resulting slurry is cooled to 5–10° C and the solid is recovered by filtration, washed with water and dried to obtain 39.0 grams (77% of theoretical) of the desired product (m.p. 88–90° C).

In the manner described above substituting methanol, isopropanol, or n-butanol for the ethanol the corresponding dimetyl, diisopropyl and di-n-butyl esters of N-(p-methylaminobenzoyl)glutamic acid are similarly obtained.

In the manner described above substituting zinc N-(p-aminobenzoyl)-L-(+)-glutamate for the zinc N-(p-methylaminobenzoyl)-L-(+)-glutamate, diethyl (p-aminobenzoyl)-L-(+)-glutamate is obtained. The zinc N-(p-aminobenzoyl)-L-(+)-glutamate can be prepared by the procedure of Example 2 of U.S. Pat. No. 3,892,801.

I claim:

1. A process for the preparation of an ester represented by formula (I):

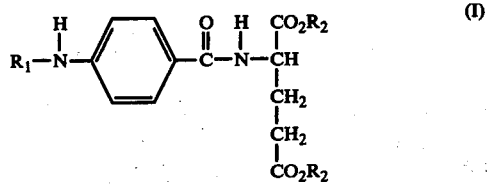

wherein $R_1$ is hydrogen or $C_1$–$C_4$ alkyl and $R_2$ is $C_1$–$C_4$ alkyl, which comprises reacting a zinc salt of an acid represented by formula (II):

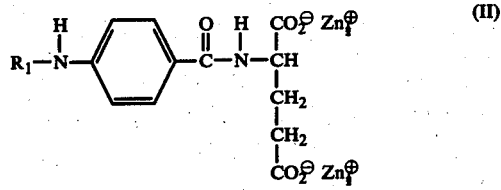

wherein $R_1$ is as previously identified, with a $C_1$–$C_4$ alcohol at ambient temperature in the presence of an inorganic acid to form said ester of formula (I); diluting the reaction mixture with water; clarifying the diluted reaction mixture; alkalizing said clarified reaction mixture to about pH 4–6 to precipitate said ester of formula (I); and, recovering the same.

2. The process of claim 1 wherein the alkalizing agent is ammonium hydroxide and the clarified reaction mixture is adjusted to about pH 5.

3. The process of claim 2 wherein the alcohol is ethanol.

4. The process of claim 1 wherein the salt is zinc N-(p-methylaminobenzoyl)glutamate.

5. The process of claim 4 wherein the salt is zinc N-(p-methylaminobenzoyl)-L-(+)-glutamate.

6. The compound zinc N-(p-methylaminobenzoyl)-L-(+)-glutamate.

* * * * *